United States Patent [19]

Haber et al.

[11] Patent Number: 5,582,595
[45] Date of Patent: Dec. 10, 1996

[54] ASPIRATING SYRINGE HAVING A PLUNGER GUIDE FOR A RECIPROCATING PLUNGER ASSEMBLY

[75] Inventors: Terry M. Haber, El Toro; William H. Smedley, Lake Elsinore; Clark B. Foster, Laguna Niguel, all of Calif.

[73] Assignee: Habley Medical Technology Corporation, Lake Forest, Calif.

[21] Appl. No.: 535,718

[22] Filed: Sep. 28, 1995

[51] Int. Cl.$^6$ .................................................. A61M 5/00
[52] U.S. Cl. ........................ 604/187; 604/218; 604/227
[58] Field of Search ..................................... 604/218, 220, 604/221, 223, 233, 234, 227, 228, 187, 207–210

[56] References Cited

U.S. PATENT DOCUMENTS

| | | | |
|---|---|---|---|
| 2,863,452 | 12/1958 | Ogle, Sr. | 604/210 |
| 3,990,446 | 11/1976 | Taylor | 604/227 X |
| 4,484,915 | 11/1984 | Tartaglia | 604/227 |
| 4,518,387 | 5/1985 | Murphy et al. | 604/187 |
| 4,639,248 | 1/1987 | Schweblin | 604/218 X |
| 5,135,511 | 8/1992 | Houghton et al. | 604/220 |

*Primary Examiner*—John D. Yasko
*Attorney, Agent, or Firm*—Hawes, Fischer & Dickinson

[57] ABSTRACT

Disclosed is an aspirating syringe having a hollow barrel and a piston assembly that is adapted to move reciprocally through the barrel, whereby the barrel is first infused with a fluid medication from a standard pharmaceutical vial during an infusion step so that the medication can then be expulsed to a target tissue site during an injection step. A pair of elongated plunger guides extend axially and proximally from the barrel in parallel alignment with each other. Each of the plunger guides has a longitudinal track groove to receive a respective guide tab carried by and movable with the piston assembly. The guide tabs ride through the track grooves of the plunger guides to stabilize the reciprocal movement of the piston assembly and thereby permit the barrel to be infused with a precise volume of fluid medication. The piston assembly includes a finger grip by which the syringe may be advantageously and accurately manipulated by a health care worker using only a single hand to complete both the aspiration and injection steps.

17 Claims, 5 Drawing Sheets

ASPIRATING SYRINGE HAVING A PLUNGER GUIDE FOR A RECIPROCATING PLUNGER ASSEMBLY

BACKGROUND OF THE INVENTION

1. Field of the Invention

This invention relates to syringe having a plunger guide that is adapted to stabilize the reciprocal movement of a plunger assembly and facilitate the manipulation of the syringe during fluid aspiration and injection steps completed by a health care worker and requiring the use of only one hand.

2. Background Art

Prior to the administration of an injection, the syringe that delivers the injection to a target tissue site is infused with fluid (e.g. medication) stored in a pharmaceutical vial by means of a needle cannula that penetrates the septum of the vial. A health care worker typically cradles the barrel of the syringe with one hand while using the other hand to retract the plunger assembly proximally through the barrel, whereby the complete the fluid aspiration step. The injection is then administered as the health care worker drives the plunger assembly distally through the barrel to expulse the fluid contents thereof into the target tissue site.

During the fluid aspiration step, it is common for the hand of the heath care worker which cradles the syringe barrel to also cover the usual calibration lines printed thereon, such that said lines are partially or totally obscured. Consequently, the syringe barrel may be overfilled with fluid from the pharmaceutical vial. What is more, the retraction of the piston assembly during the fluid aspiration step is frequently characterized by an unstable ride caused by the arm movement of the health care worker. The foregoing results in the inability of the health care worker to accurately infuse the syringe barrel with a precise volume of fluid from the vial and further contributes to overfilling the barrel. Accordingly, the excess fluid is often expulsed from the syringe barrel and discarded prior to the injection step. As will be appreciated by those skilled in the art, discarding the excess fluid can result in inefficiency and waste, particularly when the fluid is very expensive to manufacture and/or rare in availability.

It would therefore be desirable to have an aspirating syringe that can be reliably manipulated by a health care worker so that the syringe barrel will be accurately filled with a precise volume of fluid, whereby to eliminate the waste and inefficiency commonly associated with conventional syringes.

SUMMARY OF THE INVENTION

In general terms, an aspirating syringe is disclosed having a syringe barrel, a needle cannula located at the distal end of the barrel to communicate with the fluid contents of a pharmaceutical vial, and an annular finger flange support located at the proximal end of the barrel. A pair of finger flanges project outwardly and in opposite directions from the finger flange support. In accordance with this invention, a pair of elongated, parallel aligned plunger guides are coextensively connected to and extend proximally from the finger flange support. Each plunger guide has a guide track extending axially therealong. A pair of flexible guide tabs are formed at the proximal end of a first of the plunger guides. A thumb base is pivotally connected to the proximal end of the second plunger guide by means of a living hinge. To complete the assembled syringe configuration, the thumb base is rotated at its hinge towards the first plunger guide until the guide tabs of the first plunger guide are received through a slot formed in the thumb base. Accordingly, the thumb base extends between the pair of plunger guides in spaced, parallel alignment with the finger flange support.

A plunger assembly is received in and adapted for reciprocal movement through the syringe cylinder during aspirating and injecting steps. The plunger assembly includes an elongated plunger stem, a plunger head located at the distal end of the stem, and a plunger control base located at the proximal end of the stem. A pair of finger ledges extend outwardly and at opposite directions from the plunger control base. A pair of guide tabs also extend outwardly and in opposite directions from the plunger control base. In the assembled syringe configuration, the guide tabs ride through respective guide tracks in the plunger guides to stabilize the reciprocal movement of the piston assembly through the syringe barrel and enable the barrel to be accurately filled with a precise volume of fluid.

In operation, the syringe is manipulated in the aspirating step when a health care worker places his thumb against the thumb base and his forefinger and middle finger against the finger ledges. The health care worker then pulls the finger ledges proximally towards the thumb base, whereby the piston assembly is correspondingly moved proximally through the syringe barrel so that the barrel is infused with fluid from the pharmaceutical vial. At the conclusion of the aspirating step, the syringe is manipulated in the injection step by the health care worker relocating his thumb to the plunger control base and his forefinger and middle finger to the finger flanges. The health care worker then pushes the plunger control base distally towards the finger flanges, whereby the piston assembly is correspondingly moved distally through the syringe barrel so that the fluid is expulsed from the barrel to a target tissue area via the needle cannula.

DETAILED DESCRIPTION

Figure 1:
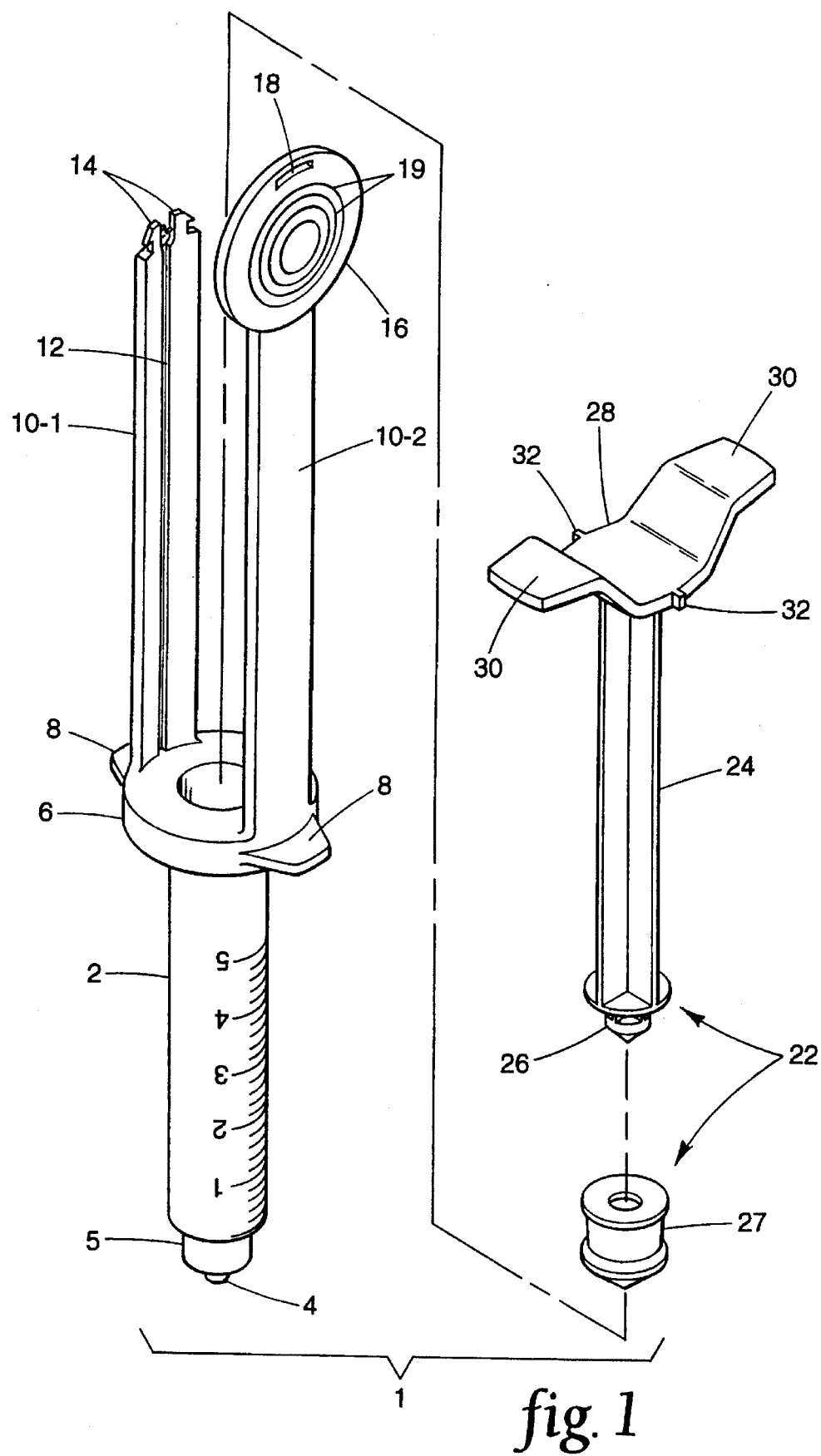
FIG. 1 is an exploded view of the aspirating syringe which forms the present invention having a plunger guide for a reciprocating plunger assembly.
Figure 2:
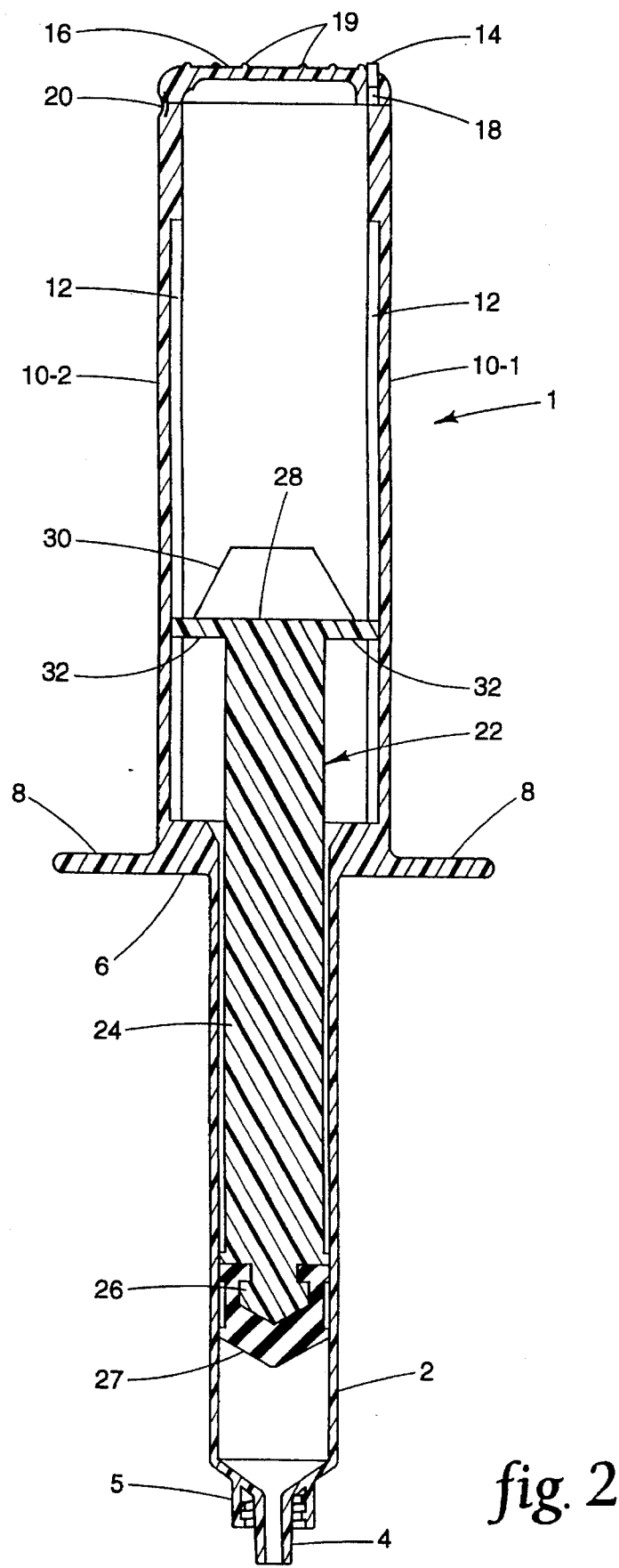
FIG. 2 is a cross-section of the aspirating syringe of FIG. 1 in the assembled syringe configuration.

The aspirating syringe 1 which forms the present invention is best described while referring initially to FIGS. 1 and 2 of the drawings. Aspirating syringe 1 includes a conventional glass or plastic syringe barrel 2 with the usual calibration lines printed along the side thereof. At the distal end of the syringe barrel 2 is a standard needle hub 4 surrounded by a Luer lock fitting 5 to which a needle cannula (designated 34 in FIGS. 5 and 6) is removably attached. Located at the proximal end of the barrel 2 is an annular finger flange support 6. A pair of finger flanges 8 extends outwardly and in opposite directions from the finger flange support 6 to enable a health care worker to reliably grasp and manipulate the syringe 1 during the injection step in a manner to be described in greater detail when referring specifically to FIG. 6.

In accordance with the present invention, a pair of elongated plunger guides 10-1 and 10-2 are coextensively connected to the finger flange support 6 and extend proximally therefrom in axial alignment with the syringe barrel 2 and in parallel alignment with each other. By way of example, plunger guides 10-1 and 10-2 may be manufactured from plastic and molded to the finger flange support 6 to form a continuous one-piece assembly. Each plunger guide 10-1 and 10-2 has a track groove 12 running longitudinally therealong. Located at the proximal end of one plunger guide 10-1 is a pair of flexible locking tabs 14 having a spring-like characteristic. Located at the proximal end of the other plunger guide 10-2 is a plastic, disc-like thumb base 16. The thumb base 16 has a slot 18 formed therethrough and the usual anti-slip ridges 19 molded therein.

As best shown in FIG. 2 and as will be described in greater detail hereinafter when referring to FIGS. 3 and 4, the thumb base 16 is coextensively and pivotally connected to plunger guide 10-2 by means of a continuously molded (i.e. living) hinge 20, whereby thumb base 16 is adapted (in the assembled syringe configuration of FIG. 2) to be rotated towards the opposing plunger guide 10-2 and attached thereto by locating the locking tabs 14 of plunger guide 10-1 within the slot 18 through thumb base 16. In the assembled configuration of FIG. 2, the thumb base 16 performs an important function that enables a health care worker to grasp and manipulate syringe 1 during the aspiration step in a manner that will be described while referring specifically to FIG. 5.

Figure 5:
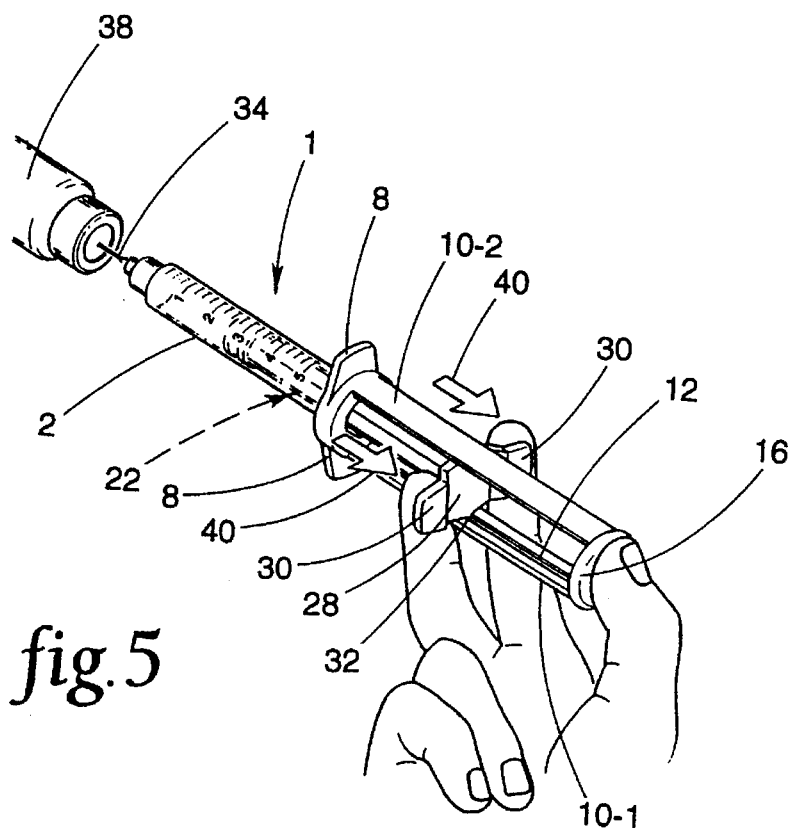
FIG. 5 shows the manipulation of the aspirating syringe during the aspirating step whereby the syringe is infused with fluid from a pharmaceutical vial.
Figure 6:
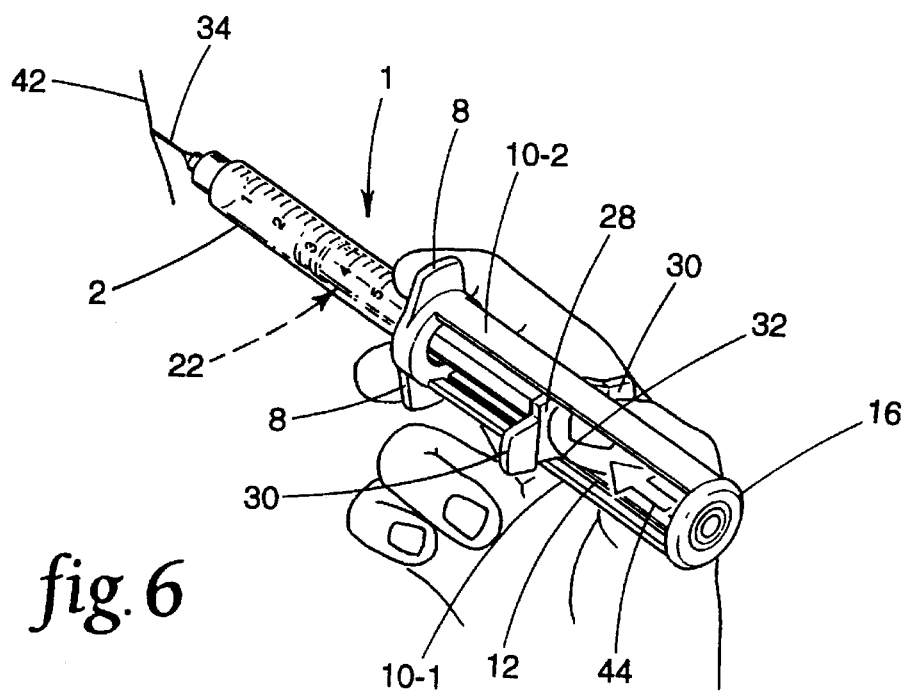
FIG. 6 shows the manipulation of the aspirating syringe during the injection step when fluid from the syringe is expulsed to a target tissue site.

The aspirating syringe 1 also includes a plunger assembly 22 that is adapted to be received within and moved reciprocally through the syringe barrel 2 during the aspiration and injection steps of FIGS. 5 and 6. Plunger assembly 22 has an elongated plunger stem 24. Projecting distally from the plunger stem 24 is a locking nub 26 that is detachably connected to the usual rubber piston 27. Plunger assembly 22 also has a plunger control base 28 located at the proximal end of plunger stem 24. Projecting laterally and in opposite directions from the plunger control base 28 is a pair of finger ledges 30. The finger ledges 30 are spaced proximally from the base 28 to receive the fingers of a health care worker thereagainst during the aspiration step of FIG. 5.

A pair of guide tabs 32 also project outwardly and in opposite directions from the plunger control base 28. In the assembled syringe configuration of FIG. 2, the guide tabs 32 are received within and adapted to ride along respective track grooves 12 of the plunger guides 10-1 and 10-2 as the plunger assembly 22 is moved reciprocally through the syringe barrel 2 during the aspiration and injection steps.

Figure 3:
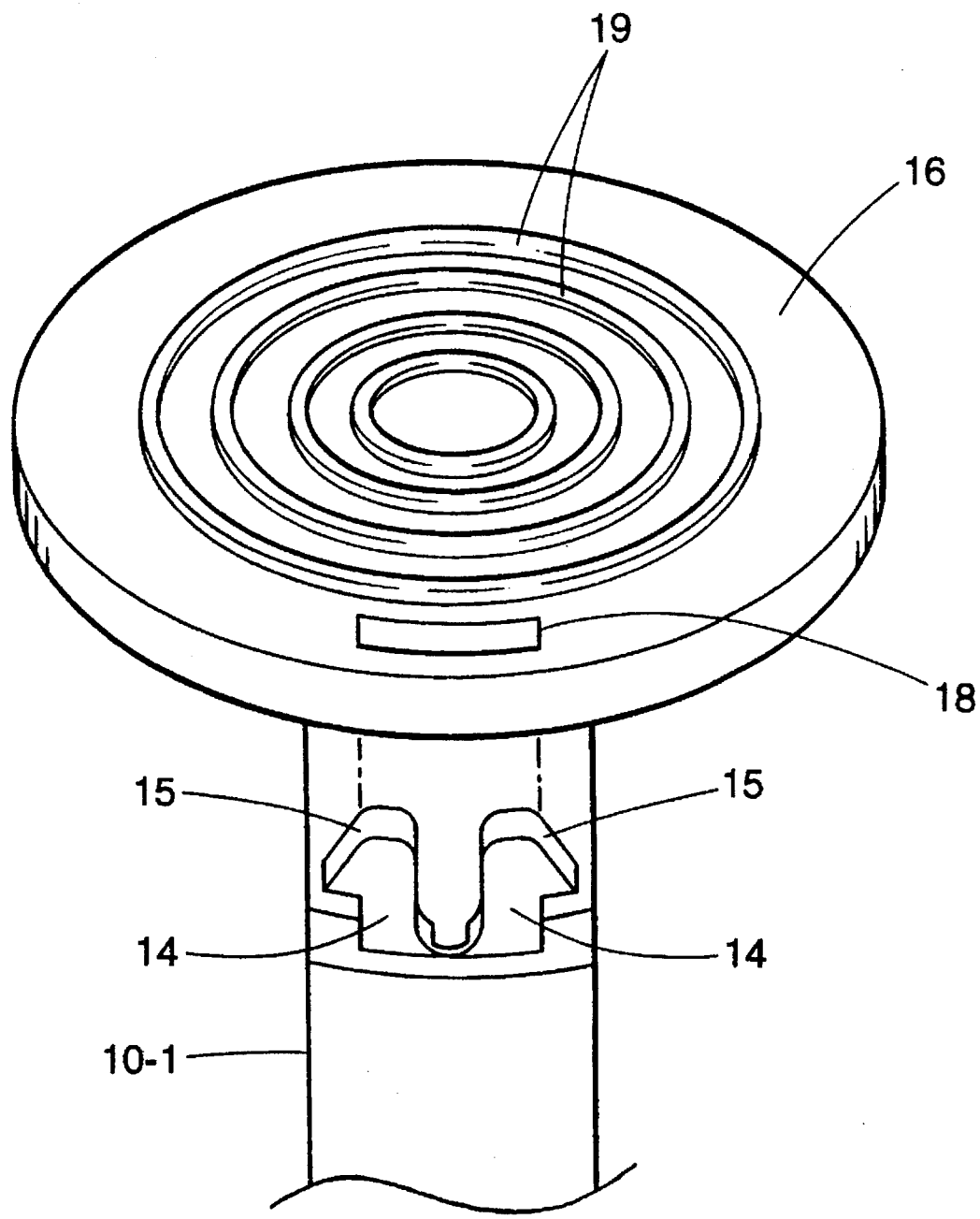
FIGS. 3 and 4 show the attachment of a thumb base to the plunger guide of the aspirating syringe.
Figure 4:
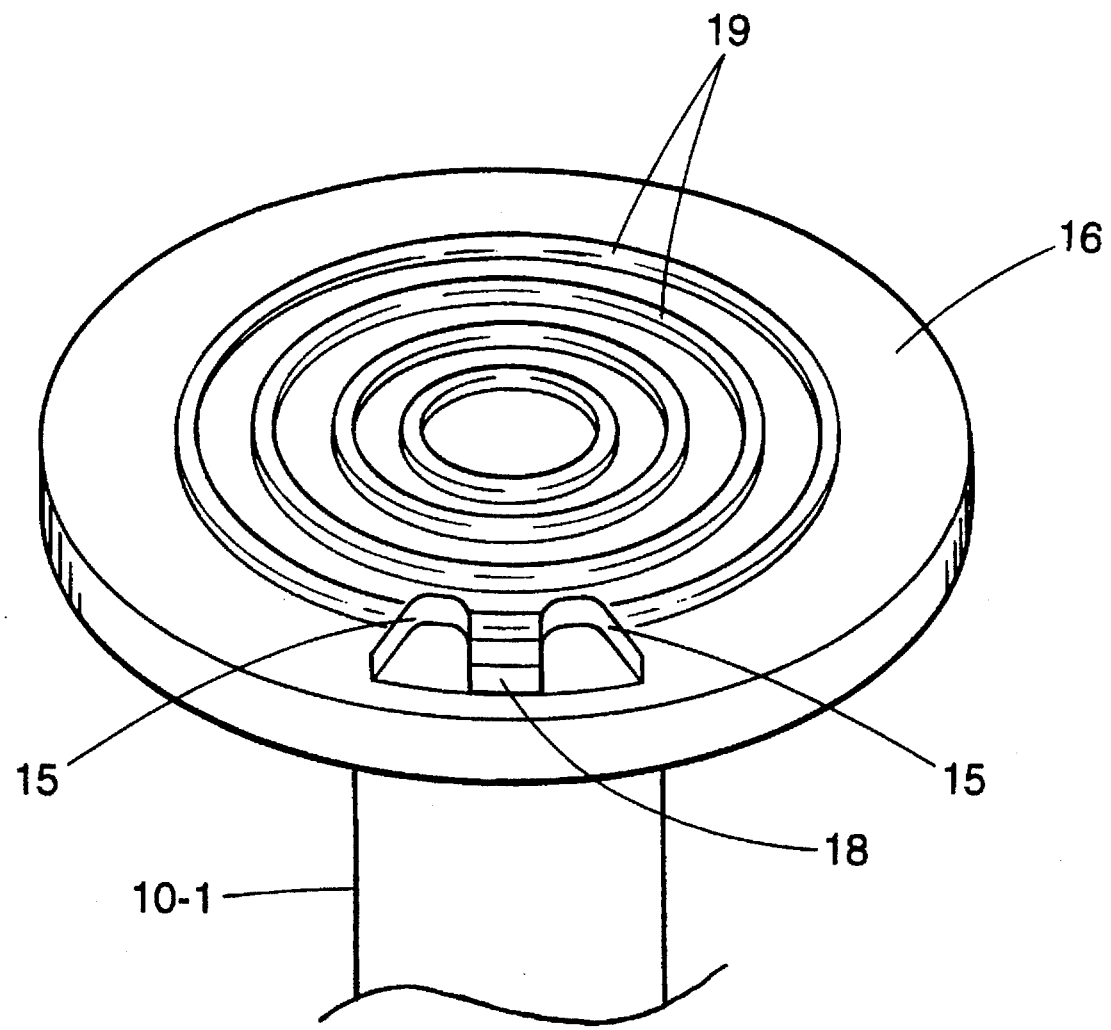

Turning now to FIGS. 3 and 4 of the drawings, the aspirating syringe 1 is described as the thumb base 16 of plunger guide 10-2 is rotated around its living hinge (designated 20 in FIG. 2) so as to be fixedly attached to the opposing plunger guide 10-1. More particularly, the thumb base 16 is rotated towards the plunger guide 10-1 (best shown in FIG. 3) until the flexible locking tabs 14 projecting from plunger guide 10-1 are received in the slot 18 formed through the thumb base 16 (best shown in FIG. 4). The locking tabs 14 will be slightly stressed and flexed towards one another to enable tabs 14 to be accommodated by the slot 18. Once the locking tabs 14 pass completely through the slot 18, they will move away from one another (i.e. return to their original unstressed, at-rest positions).

Each locking tab 14 is shown having an associated hook portion 15 (best shown in FIG. 3) by which to capture the thumb base 16 to prevent the locking tabs 14 from being pulled out of slot 18 and the thumb base 16 from rotating out of attachment to plunger guide 10-1. With the thumb base 16 rotated into attachment with the plunger guide 10-1 in the assembled syringe configuration shown in FIG. 2, the thumb base 16 will be retained in spaced, parallel alignment with the finger flange support 6 across opposite ends of the pair of plunger guides 10-1 and 10-2.

The operation of the aspirating syringe 1 of this invention is now described during the aspirating and injecting steps while referring to FIGS. 5 and 6 of the drawings. FIG. 5 shows a needle cannula 34 attached to the distal end of the syringe barrel 2 and communicating with the fluid contents of a conventional pharmaceutical vial 38 through the rubber septum thereof. In order that the barrel 2 can be infused with fluid (e.g. medication) from the vial 38 during the aspiration step, the forefinger and middle finger of the health care worker are placed underneath respective finger ledges 30 adjacent the plunger control base 28. At the same time, the thumb of the health care worker is placed atop the thumb base 16.

With the health care worker's thumb braced against the thumb base 16, an axial pulling force is exerted by the forefinger and middle finger against the finger ledges 30. Accordingly, the plunger assembly 22 is moved proximally through the barrel 2 (in the direction of the reference arrows 40 of FIG. 5), whereby the barrel is infused with fluid via cannula 34 by means of suction. As the plunger assembly 22 is moved in the proximal direction, the guide tabs 32 projecting from the plunger control base 28 ride through the track grooves 12 in the opposing plunger guides 10-1 and 10-2 to insure a smooth travel of the plunger assembly. By virtue of the foregoing, the aspirating syringe 1 may be accurately infused with a precise volume of fluid from pharmaceutical vial 38. That is, the health care worker need only use a single hand to complete the aspirating step such that the plunger assembly 22 may be displaced in the proximal direction through syringe barrel 2 while providing the health care worker an unobstructed view of the calibration lines printed on the barrel 2.

FIG. 6 shows the aspirating syringe 1 during the injection step when the fluid with which the syringe barrel 2 has been filled is expulsed via cannula 34 to the target tissue site 42. To accomplish the foregoing, the health care worker relocates his thumb from the thumb base 16 (as shown in FIG. 5) to the plunger control base 28. Next, while maintaining thumb contact with plunger control base 28, the health care worker relocates his forefinger and middle finger from the finger ledges 30 (as shown in FIG. 5) to the finger flanges 8. It may be appreciated that the health care worker may relocate his thumb and fingers to initiate the injection step of FIG. 6 by using only a single hand. That is to say, and unlike conventional syringes, the syringe 1 of the present invention can be advantageously manipulated in both the aspiration and injection steps without the health care worker having to use one hand to grasp the syringe barrel 2 and a second hand to operate the plunger assembly 22.

To complete the injection step of FIG. 6, the health care worker braces his forefinger and middle finger against the finger flanges 8 and applies an axial pushing force against the plunger control base 28. Accordingly, the plunger assembly 22 is moved distally through the barrel 2 (in the direction of the reference arrow 44), whereby fluid is expulsed from the syringe 1 into the target tissue site 42. As the plunger assembly 22 is moved in the distal direction, the guide tabs 32 projecting from plunger control base 28 ride distally through the track grooves 12 in the opposing plunger guides 10-1 and 10-2 to insure a smooth and stable travel of the plunger assembly. The injection may now be completed in the usual manner.

While a preferred embodiment of this invention has been shown and disclosed, various modifications and changes may be made without departing from the true spirit and scope of this invention.

Having set forth the preferred embodiment, what is claimed is:

1. A syringe comprising:

a hollow barrel having a longitudinally extending axis and proximal and distal ends, said barrel including means located at the distal end thereof by which to couple said barrel to a needle cannula, said barrel also including a pair of finger receiving flanges projecting laterally from the proximal end thereof;

at least a first plunger guide extending from the proximal end of said barrel in axial alignment with said barrel, said first plunger guide having a first guide track extending longitudinally therealong;

a plunger assembly moving proximally and distally relative to said barrel and including a plunger stem having first and second ends, a plunger head located at the first end of said plunger stem and movable within said barrel, and finger grip means located at the second end of said plunger stem by which to control the movement of said plunger assembly, said finger grip means including a control base extending laterally across the second end of said plunger stem and sized to receive the thumb of a user thereagainst, and a pair of finger ledges connected to and extending in opposite directions relative to one another from said control base, each of said pair of finger ledges sized to receive a finger of the user thereagainst; and at least a first guide tab connected to and projecting from the control base of said finger grip means to be received in and ride through said first guide track of said first plunger guide to stabilize said plunger assembly as said plunger assembly moves proximally and distally relative to said barrel.

2. The syringe recited in claim 1, further comprising a second plunger guide extending from the proximal end of said barrel in axial alignment with said barrel and in parallel alignment with said first plunger guide, said second plunger guide having a second guide track extending longitudinally therealong.

3. The syringe recited in claim 2, wherein said plunger assembly also includes a second guide tab to be received in and ride through said second guide track of said second plunger guide to stabilize said plunger assembly as said plunger assembly moves proximally and distally relative to said barrel.

4. The syringe recited in claim 3, wherein said first and second guide tabs that project from said plunger assembly to be received in and ride through said first and second guide tracks of said first and second plunger guides are connected to and extend outwardly and in opposite directions relative to one another from said finger grip means.

5. The syringe recited in claim 3, wherein each of said first and second plunger guides has a first end connected to the proximal end of said barrel and an opposite end spaced proximally from said barrel, said syringe further comprising a thumb base sized to receive the thumb of a user thereagainst and extending between the opposite ends of said first and second plunger guides.

6. The syringe recited in claim 5, wherein said thumb base is pivotally attached to the opposite end of one of said first and second plunger guides and adapted to be rotated towards and into engagement with the opposite end of the other of said first and second plunger guides.

7. The syringe recited in claim 6, wherein said thumb base is pivotally attached to the opposite end of the one of said first and second plunger guides by means of a living hinge extending continuously between said thumb base and said one plunger guide.

8. The syringe recited in claim 6, wherein the opposite end of the other of said first and second plunger guides has a locking tab extending therefrom and said thumb base has a slot formed therein, said locking tab received within said slot when said thumb base is rotated toward and into engagement with the opposite end of said other plunger guide to retain said thumb base extending between the opposite ends of said first and second plunger guides.

9. The syringe recited in claim 3, wherein said first and second plunger guides are integrally and coextensively connected to the proximal end of said barrel to form a single continuous syringe assembly with said barrel.

10. The syringe recited in claim 1, wherein said first guide track is a groove formed in and extending longitudinally along said first plunger guide.

11. The syringe recited in claim 2, wherein said second guide track is a groove formed in and extending longitudinally along said second plunger guide.

12. A syringe comprising:

a hollow barrel having a longitudinally extending axis and proximal and distal ends, said barrel including means located at the distal end thereof by which to couple said barrel to a needle cannula, said barrel also including a pair of finger receiving flanges projecting laterally from the proximal end thereof;

first and second plunger guides extending from the proximal end of said barrel in axial alignment with said barrel and in parallel alignment with each other, each of said first and second plunger guides having a respective guide track extending longitudinally therealong;

a plunger assembly moving proximally and distally relative to said barrel and including a piston stem having first and second ends, a plunger head located at the first end of said plunger stem and movable within said barrel, and grip means located at the second end of said plunger stem by which to control the movement of said plunger assembly, said grip means including a control base at the second end of said plunger stem and sized to receive the thumb of a user thereagainst and a pair of finger ledges connected to and extending from said base, each of said pair of finger ledges sized to receive a finger of the user thereagainst; and first and second guide tabs carried by and moving with said piston assembly, said first and second guide tabs received in and riding through said respective guide tracks of said first and second plunger guides to stabilize said plunger assembly as said plunger assembly moves proximally and distally relative to said barrel.

13. The syringe recited in claim 12, wherein said first and second guide tabs to be received in and ride through said respective guide tracks of said first and second plunger guides project outwardly from said control base of said grip means in opposite directions relative to one another.

14. The syringe recited in claim 12, further comprising a thumb base extending laterally between said first and second plunger guides in spaced parallel alignment with said pair of finger receiving flanges projecting laterally from the proximal end of said barrel, said thumb base sized to receive the thumb of the user thereagainst.

15. The syringe recited in claim 12, wherein the respective guide tracks of said first and second plunger guides are grooves formed therein and extending longitudinally therealong.

16. A syringe comprising:
   a hollow barrel having a longitudinally extending axis and proximal and distal ends, said barrel including means located at the distal end thereof by which to couple said barrel to a needle cannula, said barrel also including a pair of finger receiving flanges projecting laterally from the proximal end thereof;
   at least a first plunger guide extending from the proximal end of said barrel in axial alignment with said barrel, said first plunger guide having a first groove formed therein and extending longitudinally therealong; and
   a plunger assembly moving proximally and distally relative to said barrel and including a plunger stem having first and second ends, a plunger head located at the first end of said plunger stem and movable within said barrel, and finger grip means located at the second end of said plunger stem by which to control the movement of said plunger assembly, said plunger assembly also including at least a first guide tab extending from said finger grip means to be received in and ride through said first groove of said first plunger guide to stabilize said plunger assembly as said plunger assembly moves proximally and distally relative to said barrel.

17. The syringe recited in claim 16, further comprising a second plunger guide extending from the proximal end of said barrel in axial alignment with said barrel and in parallel alignment with said first plunger guide, said second plunger guide having a second groove formed therein and extending longitudinally therealong, said plunger assembly also including a second guide tab extending from said finger grip means to be received in and ride through said second groove of said second plunger guide to stabilize said plunger assembly as said plunger assembly moves proximally and distally relative to said barrel.

* * * * *